United States Patent [19]

Mittleman

[11] Patent Number: 4,581,020
[45] Date of Patent: Apr. 8, 1986

[54] MEDICATION DELIVERY DEVICE AND SYSTEM FOR PERCUTANEOUS ADMINISTRATION OF MEDICATION

[75] Inventor: Herbert Mittleman, Deerfield, Ill.

[73] Assignee: Trimedyne, Inc., Santa Ana, Calif.

[21] Appl. No.: 514,572

[22] Filed: Jul. 18, 1983

[51] Int. Cl.⁴ .............................................. A61M 5/32
[52] U.S. Cl. ...................................... 604/175; 604/256
[58] Field of Search ................ 604/29, 165, 175, 283, 604/905, 99, 256

[56] References Cited

U.S. PATENT DOCUMENTS

| | | | |
|---|---|---|---|
| 3,310,048 | 3/1967 | Ewing | 604/175 |
| 3,765,032 | 10/1973 | Palma | 604/175 |
| 3,795,246 | 3/1974 | Sturgeon | 604/99 |
| 4,161,949 | 7/1979 | Thanawalla | 604/905 |
| 4,298,001 | 11/1981 | Hargest, III et al. | 604/905 |
| 4,306,976 | 12/1981 | Bazzato | 604/29 |
| 4,315,513 | 2/1982 | Nawash et al. | 604/175 |
| 4,344,435 | 8/1982 | Aubin | 604/175 |
| 4,405,319 | 9/1983 | Cosentino | 604/175 |
| 4,405,320 | 9/1983 | Cracauer et al. | 604/175 |
| 4,416,657 | 11/1983 | Berglund | 604/29 |
| 4,417,888 | 11/1983 | Cosentino et al. | 604/29 |
| 4,419,094 | 12/1983 | Patel | 604/165 |
| 4,425,119 | 1/1984 | Berglund | 604/175 |

*Primary Examiner*—C. Fred Rosenbaum
*Assistant Examiner*—Michelle N. Lester

[57] ABSTRACT

An implantable medical device and system for percutaneous (e.g., peritoneal as well as subcutaneous) administration of a medication from an external source is disclosed. Continuous, variable rate, or intermittent administration of medication can be effected without the need for repeated puncturing of the patient's skin. The present device includes an implant that is transcutaneously anchored to the patient, an insert releasably mounted on the implant, and a seal means on the implant which seals an implant cavity that receives the insert upon removal of the insert so that the patient is protected from infection while the insert is replaced.

38 Claims, 5 Drawing Figures

MEDICATION DELIVERY DEVICE AND SYSTEM FOR PERCUTANEOUS ADMINISTRATION OF MEDICATION

TECHNICAL FIELD OF THE INVENTION

The present invention relates to medical devices and systems which are implanted in a patient for percutaneous, especially peritoneal, delivery of medication.

BACKGROUND OF THE INVENTION

Certain medications are more effective when they are administered to a patient by injection. One such medical condition which shows improved treatment with several daily injections is the treatment of diabetes with insulin. Unfortunately, the required multiple injections not only cause physical and psychological pain, but also raise the possibility of infection.

Various pump devices have been proposed to either slowly administer a continuous flow of insulin or provide several intermittent injections over time. These devices generally use a needle, which is inserted through the skin. Due to the threat of infection, the needle must be discarded after use, and a new needle inserted in a different location each day. To meet these problems, catheters have been designed for implantation through the skin to deliver the insulin. Unfortunately, such catheters have their own shortcomings and can sometimes become infected, thrombose or become clogged, reducing or stopping the flow of insulin. Occasionally, without any apparent reason, the subcutaneous tissue of a diabetic patient will begin to degrade and inactivate insulin, reducing its usefulness.

To solve these problems, implantable insulin infusion devices have been proposed. Such devices are implanted under the skin, with a tube leading into the peritoneal cavity. This avoids the difficulties of insulin inactivation by subcutaneous tissue, clogging and the threat of thrombosis. It has also been found that insulin administered intraperitoneally is quickly carried to the liver, the natural delivery point for insulin produced by the pancreas. This form of administration also has the side benefit of minimizing ketosis and hyperglycemia.

The devices which have been proposed for such administration have a pierceable septum which is either outside the patient or is located immediately below the surface of the patient's skin. However, in attempting to solve one problem, a new problem is created. After the pierceable septum of such a device becomes worn through use, it must be surgically removed and replaced, thereby exposing the patient to pain, discomfort and possible infection. No means is provided for replacing the septum after it has become worn through repeated injections. Nor is any means provided to protect the patient from infection during such a replacement.

Accordingly, it would be desirable to provide a device and medication delivery system which avoids the shortcomings of the prior art, yet provides for a safe and effective way of delivering a medication to the patient percutaneously. Such a device and system should have parts which can be easily and safely replaced as they become worn through use and should also protect the patient against infection while a part is being replaced. Means should also be provided for connecting with a pump for continuous administration of medication. The present invention meets these desires.

SUMMARY OF THE INVENTION

The present invention is a medical device and system for transcutaneous implantation in a patient which permits percutaneous (e.g., peritoneal as well as subcutaneous) administration of a medication from an external source. The medical device and system allow for continuous, variable rate or intermittent administration of medication, as desired, without need for repeated puncturing of the skin. The medical device serves as a "painless injection site" and avoids the physical and psychological trauma which can be caused by repeated injections, while protecting the patient from infection. The medical device of this invention is particularly well suited for use as a peritoneal access device.

The present medical device generally includes an implant which is transcutaneously anchored in the patient, e.g., by means of felt cuffs, an insert which is releasably mounted on the implant, seal means carried by the implant which protects the patient from infection when the insert is removed from the implant. The implant has a supracutaneous portion which remains exposed above the skin of the patient, and a subcutaneous portion which is adapted to be placed below the skin of the patient. The subcutaneous portion defines a duct in fluid communication with the patient's peritoneal cavity or other desired region, and through which the medication is administered.

The insert is releasably and sealably mounted on the supracutaneous portion and is partially exposed outside the patient. The insert includes medication accepting means such as a pierceable and resealing septum for placing the duct in sealed fluid communication with the medication source such as a syringe having a hollow needle. The insert also coacts with the seal means. As the system becomes worn or a different configuration is desired, the insert can easily be replaced without having to surgically remove the entire device. This greatly simplifies use of the device and reduces patient discomfort.

The insert preferably includes a tubular body member having a proximal end and a distal end and defining a passageway along its length. The pierceable and resealing septum seals the passageway by being mounted on the proximal end. The words "proximal" and "distal" are used with respect to the perspective of the physician as opposed to the patient in which the device is implanted. The insert preferably is also provided with a flange extending about the proximal end of the tubular member for cooperating and sealing with the supracutaneous portion of the implant. The insert preferably is retained on the implant by appropriate locking means such as a latch on the insert body member which latch is received in a detent defined by the implant.

The seal means coacts with the insert such that when the insert is removed from the implant, the seal means seals the duct from the ambient surroundings outside the patient. Thus, the seal means automatically protects the patient during the period while an insert with a worn septum is removed and a new insert is affixed. The seal means preferably is a closure having a generally frustoconical side wall which matingly cooperates with a sealing surface defined by the implant. The closure is positioned in a cavity defined by the implant and is biased against a sealing surface by a biasing means such as a coil spring, leaf spring, or the like.

The present invention also includes a medication delivery system to facilitate continuous, variable rate or intermittent administration of medication by the use of a pump or similar device operably connected to a medication reservoir. The medication delivery system of the present invention includes a connector assembly outside the patient which is releasably attached to the medical device.

The connector assembly generally includes hollow piercing means such as a needle mounted on a housing in fluid communication with an inlet defined by the housing. The inlet is adapted to be placed in fluid communication with the medication reservoir or pump through an appropriate length of tubing. The connector assembly is releasably mounted on the supracutaneous portion of the implant such that the piercing means penetrates the septum of the insert and allows for delivery of the medication through the duct to the patient.

To facilitate such mounting, the connector assembly is preferably provided with attachment means such as a coupling member which releasably grips a collar defined about the periphery of the supracutaneous portion of the implant. The coupling member preferably has a limited lateral float relative to the piercing means to allow for proper alignment of the piercing means with the septum. This insures a proper seal with the septum and also prevents undue damage to the septum.

DETAILED DESCRIPTION OF THE PREFERRED EMBODIMENTS

Figure 1:
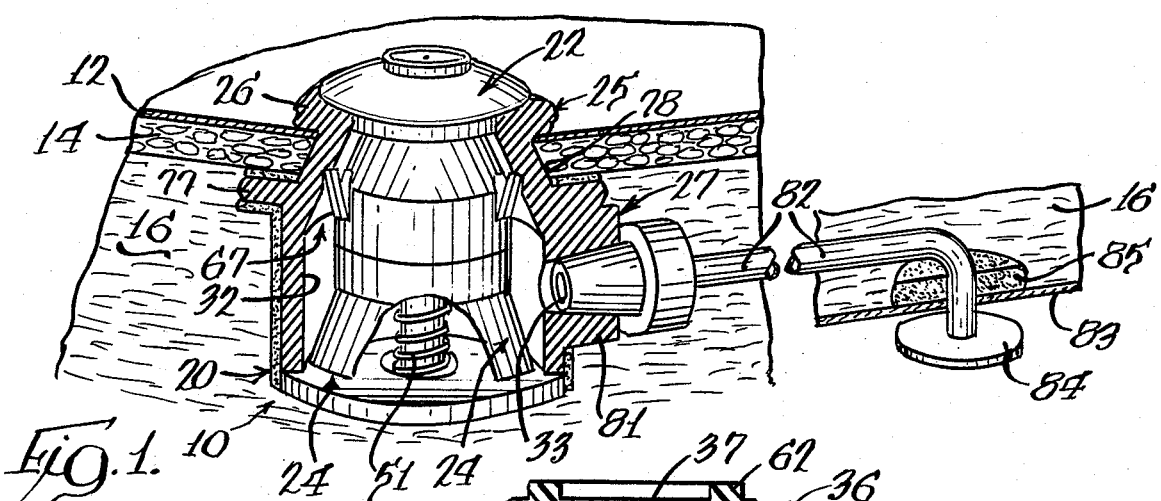
FIG. 1 is a perspective view, partly broken away, showing a medical device of the present invention positioned through the skin of a patient and including an insert mounted on an implant and seal means within the implant.

While this invention can be embodied in many different forms, there are shown in the drawings and described in detail, preferred embodiments of the invention. The present disclosure is an exemplification of the principles of the invention and is not intended to limit the invention to the embodiments illustrated.

The present invention is a medical device and system which allow for the painless direct administration of medication into a patient. After the medical device has been surgically implanted, medication can be continuously or intermittently administered to the patient at a selected region without further pain or discomfort. In addition, the present invention allows for the easy and safe replacement of a part which may become worn through extensive use.

The advantages provided by the present device are many. For instance, it is now generally accepted that insulin administered via the peritoneal fluid permits better glucose control than insulin that is administered subcutaneously. This device is particularly well suited as a peritoneal access device for the delivery of insulin as well as other medication. Moreover, the device of this invention is also well suited for subcutaneous delivery of medication and delivery of medication to a particular body region as will be discussed in more detail below.

Figure 2:
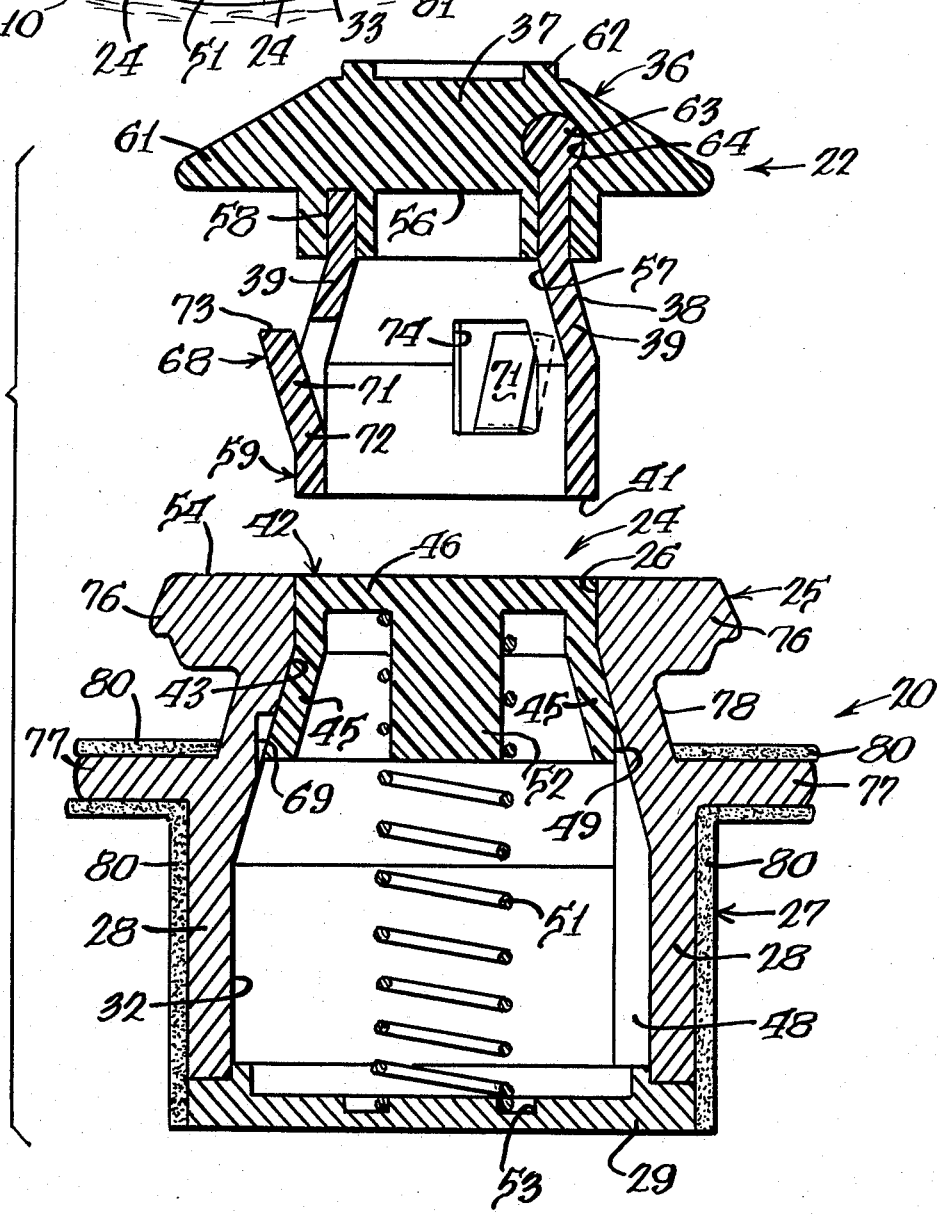
FIG. 2 is an exploded cross-sectional view of the medical device of FIG. 1 showing the insert removed from the implant and the seal means in a position closing the implant.
Figure 3:
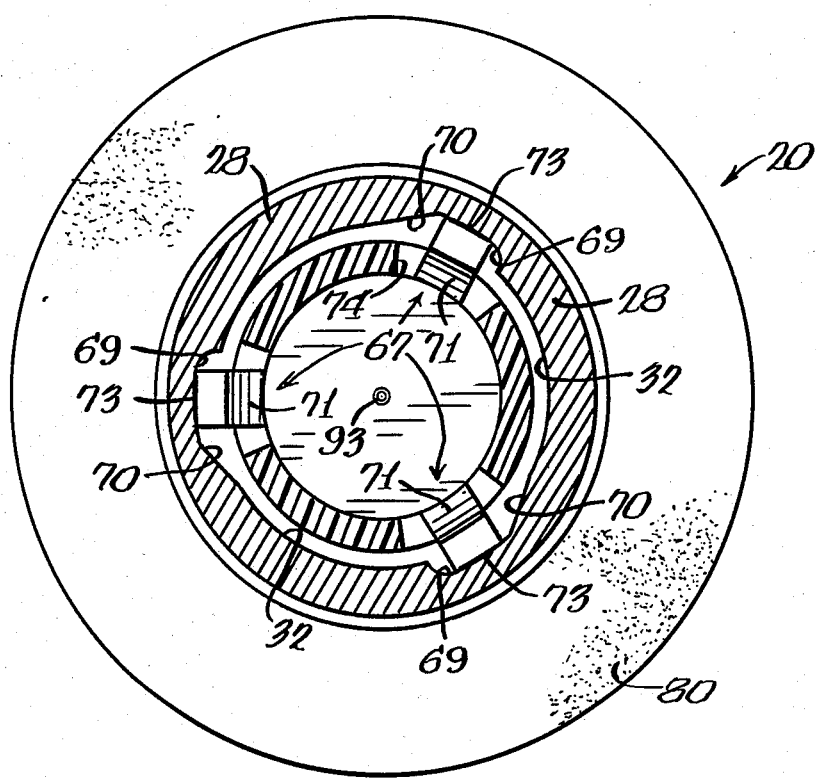
FIG. 3 is a cross-sectional view taken generally along plane 3—3 of FIG. 5 showing the internal structure of the implant.

A medical device 10 embodying the present invention is shown in FIG. 1. The device 10 is implanted transcutaneously through the epidermis and dermis 12, the subcutaneous fatty tissue 14 and into the abdominal muscle 16. Referring to FIGS. 1-3, the medical device 10 of the present invention includes an implant 20, an insert 22 which is sealingly and releasably mounted on the implant and seal means 24 carried by the implant 20. The seal means 24 coacts with the insert 22 to seal a cavity defined by the interior of the implant 20 from the ambient surroundings outside the patient when the insert is removed from the implant. The implant 20 has a supracutaneous portion 25 which defines a seat 26, and a subcutaneous portion 27 having a side wall 28 and bottom plate 29 defining the cavity 32 in fluid communication with seat 26. The subcutaneous portion 27 also defines a duct 33 in fluid communication with the cavity 32.

The implant 20 is adapted for implantation in a patient with the duct 33 in fluid communication, e.g., with the peritoneal cavity, of the patient and the supracutaneous portion 25 exposed outside the patient. The supracutaneous portion 25 remains adjacent the patient's skin and provides a generally flush appearance which is not only cosmetically desirable, but also reduces the chances of accidental disengagement. The supracutaneous portion may also be made of a skin-like color for cosmetic purposes.

The insert 22 is releasably and sealingly mounted on the implant supracutaneous portion 25. The insert 22 includes a medication accepting means 36 for placing the duct 33 in sealed fluid communication with a medication source. The medication accepting means 36 is a piercable and resealing septum 37. Septum 37 is mounted on a preferably rigid tubular-shaped body member 38 having a side wall 39 that also forms a part of the insert. A medication source such as a syringe and hollow needle can then pierce the septum 37 to deliver a desired medication throught the duct 33. Alternatively, the medication accepting means can include a tube extending from the the body member to allow connection to a pump or similar medication delivery system.

The seal means 24 is carried by the implant 20 within the cavity 32. An engagement surface 41 on the insert 22 coacts with the seal means 24 such that the seal means seals the duct 33 from the ambient surroundings outside the patient when the insert is removed from the implant. The seal means preferably includes a generally cup-shaped closure 42 biased toward and engaging a sealing surface 43 defined by the implant 20 adjacent the seat 26. The closure 42 preferably has a generally frustoconical side wall 45 about a top plate 46. The sealing surface 43 has a frustoconical shape matching the closure side wall 45.

The closure 42 is shown in FIG. 1 in its first position and in FIG. 2 in its second position. The closure 42 is biased into and maintained in the second position by appropriate biasing means such as spring 51. Any inert material of construction can be used for spring 51, such as stainless steel or nylon. To assist positioning, alignment means can be provided such as a stud 52 on the closure 42 and a groove 53 on the bottom plate 29.

When the closure 42 is in its second position and sealing the duct 33 and cavity 32 from the ambient surroundings, it is preferred that the top plate 46 is substantially planar with exterior surface 54 of the implant supracutaneous portion 25. This provides a nonobtrusive surface while protecting the patient from possible contaminants. To prevent relative rotation of the closure 42 with respect to the implant 20, the implant can be provided with an abutment 48 which cooperates with a notch 49 on the bottom portion of the closure sidewall 45.

As the insert 22 is positioned on the implant 20, the engagement surface 41 coacts with the closure 42 to move the closure against the urging of spring 51 and into its first position. The duct 33 is then in fluid communication with interior surface 56 of the septum 37 as through a passageway 57 defined by the insert body member 38. The passageway 57 preferably extends between proximal end 58 and distal end 59 of the body member 38. The tubular member 38, passageway 57, septum 37, implant 20 and closure 41 preferably have generally circular cross-sections.

To enhance sealing between the insert 22 and the implant 20, the insert can be provided with a flange 61 which extends peripherally about the proximal end 58 of the body member 38. The flange 61 contacts and seals with the external top surface 54 of the implant supracutaneous portion 25 about the seat 26. The flange 61 and septum 37 are preferably unitary and molded of a synthetic rubber material such as I010 commercially available from Tompkins Rubber Company, Blue Bell, Pennsylvania. A ridge 62 can also be provided about the septum 37 to provide a target area for the user. The unitary flange 61 and septum 37 combination can be retained on the body member 38 by one or more, usually three, knobs 63 received in sockets 64 defined by the combination.

To help retain the insert 22 on the implant 20, appropriate locking means 67 can be provided. The locking means 67 preferably includes a latch on one of the implant 20 and insert 22 and a detent on the other of the implant and insert. For ease of construction and use, the latch 68 is preferably on the insert 22 and the detent 69 is defined by the side wall 28 of the implant 20. The latch 68 preferably includes a tab 71 having a distal portion 72 mounted on the body member 38 and a proximal detent engaging portion 73 biased away from the body member wall 39. The tab 71 can be made of the same material as the body member wall 39 by cutting a generally U-shaped slot 74 in the wall 39 and bending the defined tab outwardly. The biasing of the tab results from a natural resiliency of the material forming the body member wall 39. The insert body member 38 can be made of any suitable plastic material such as acrylic, polypropylene or polycarbonate. The implant 20 and closure 42 preferably are made of the same materials.

As can best be seen in FIG. 3, the detents 69 preferably include a sloping surface 70 which leads to the surface of the wall 28 which, in turn, defines the cavity 32. Thus, as the insert 22 is rotated about one-quarter turn counter-clockwise, as shown in FIG. 3 with respect to the implant 20, the proximal detent engaging surface 73 travels along the sloped wall 70 until it disengages the detent 69 so that the locking means 67 releases the insert from the implant. This provides for simplified removal and a flat sealing surface 43. The contact of the flange 61 with the exterior surface 54 inhibits accidental rotation.

To assist in embedding the implant 20 in the patient's body, the implant 20 can be provided with a peripheral collar 76 about the supracutaneous portion 25 adapted to be located just above the skin, and a peripheral flange 77 about the subcutaneous portion adapted to be located just below the skin. The implant flange 77 and collar 76 define between them a circumferential groove 78 into which the epedermis and dermis 12 and surface fat layer 14 are received when the implant is embedded through a patient's skin. Exterior side wall 28 of the subcutaneous portion as well as the surfaces of the flange 77 can be provided with a felt material 80 to facilitate tissue ingrowth. The groove 78 can also be provided with a felt material.

In use, e.g., for peritoneal delivery of medication, the medication introduced into the implant cavity 32 enters the patient through the duct 33 defined by the subcutaneous portion 27 of the implant (FIG. 1). The duct 33 is preferably defined by a hollow boss or stem 81 extending from the sidewall 28 of the subcutaneous portion 27, and a tube 82 leading from the implant. Tube 82 preferably extends through the peritoneum 83. The far end of the tube 82 can be provided with a disc 84 to safely maintain the tube anchored into the peritoneum. A felt cuff 85 can also be provided adjacent the disc 84 to provide for tissue ingrowth and further anchoring of the far end of the tube 82. The tube 82 can also lead to another region of the patient's body, if desired.

One particular application for the medical device of the present invention is in the treatment of diabetes. For this purpose, the cavity 32 and duct 33 have a capacity equal to about one day's supply of insulin. This way, the insulin being delivered to the patient is that which was injected into the device some 24 hours earlier. Prepared according to U.S. Pharmacopeia formulation, insulin contains antibacterial agents so that any bacteria which somehow may contaminate the insulin or interior of the device will be destroyed within 24 hours. This greatly reduces the danger of peritonitis.

Figure 4:
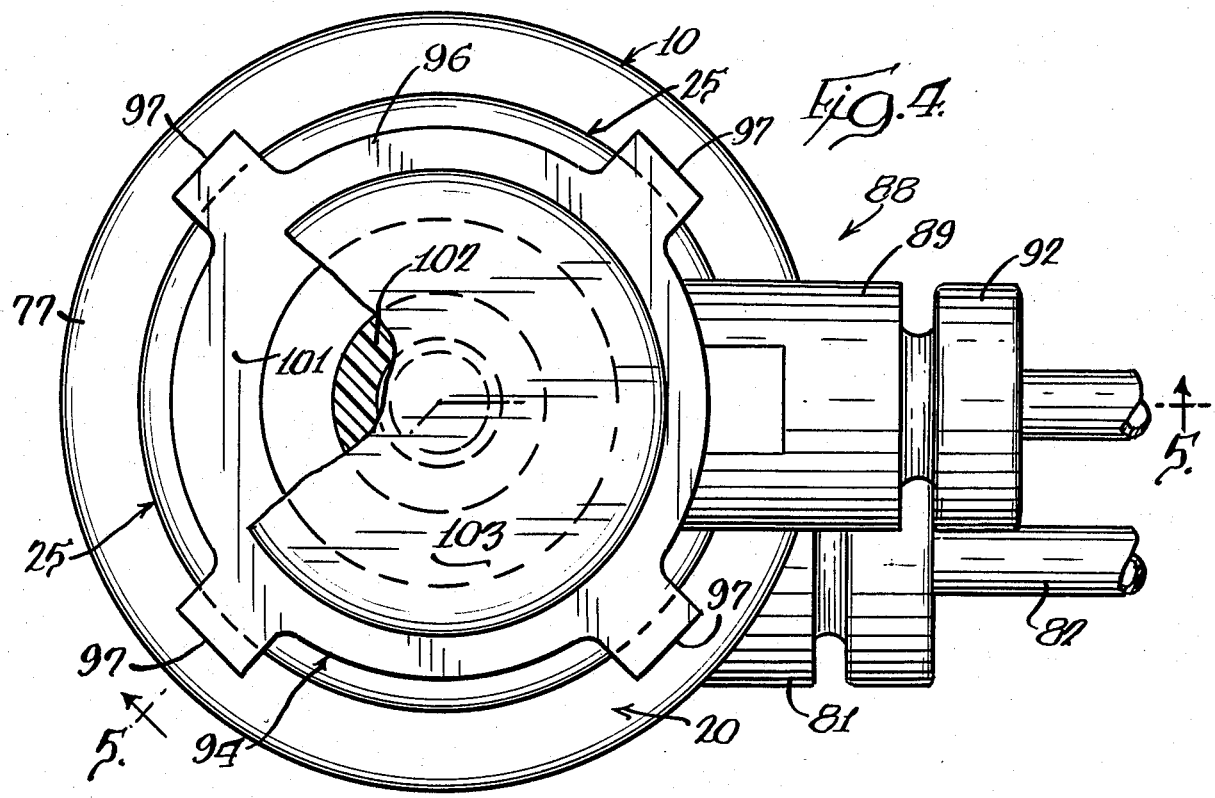
FIG. 4 is a top plan view showing a medical system embodying the present invention and including a connector assembly mounted on a medical device.
Figure 5:
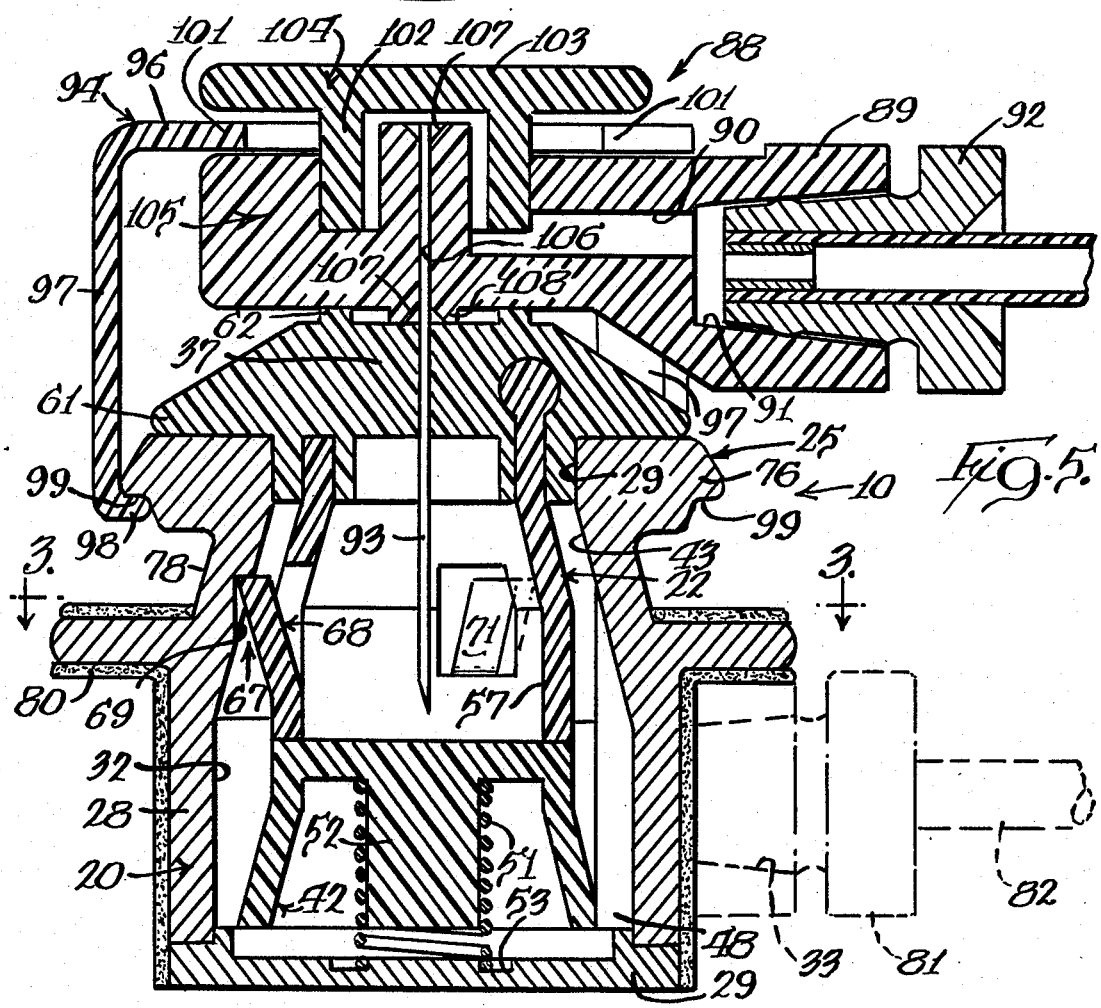
FIG. 5 is a cross-sectional view taken substantially along the planes 5—5 of FIG. 4 and showing the internal structure of the medical device and the connector assembly.

A further embodiment to the present invention is a medication delivery system as shown in FIGS. 4 and 5. Generally, the medication delivery system includes a connector assembly 88 releasably attached to the medical device 10. The connector assembly 88 includes the housing 89 which defines a channel 90 in fluid communication with an inlet 91 adapted to be placed in fluid communication with a medication reservoir or pump system (not shown) such as by fluid connector 92. The pump system can be of any medically suitable type such as a peristaltic pump connected to a collapsible medication reservoir. The connector assembly also includes a hollow piercing member such as a needle 93 in fluid communication with the channel 90 and mounted on the housing 89. The connector assembly 88 also includes attachment means 94 for releasably mounting the connector assembly on the medical device with the needle 93 penetrating the septum and placing the inlet 91 in fluid communication with the duct 33.

The attachment means 94 preferably includes a coupling member 96 having a plurality of legs 97, usually four, with catches 98 which engage a shoulder 99 about the collar 76 of the implant supracutaneous portion 25. The legs 97 preferably are spaced about and extend downwardly from a ring 101. The ring circumscribes but is spaced from a post 102 extending upward from the remainder of the housing 89. This provides limited relative lateral movement of the coupling assembly 96 with respect to the housing 89.

Should the needle 93 not be placed in the exact center of the septum 37, the ring 101 allows the housing 89 to align with the needle 93 to avoid bending the needle, tearing the septum, or possibly creating a broken channel through the septum which could cause contamination. To maintain the ring 101 about the post 102, an end plate 103 is provided above the ring on the post 102. Generally the space between the end plate 103 and the housing 89 should be greater than the thickness of the ring to allow a limited amount of tilting of the housing 89 with respect to the insert implant to also assist in aligning the housing with the needle 93 as it is inserted through the septum 37. The ridge 62 about the septum 37, together with projections 108 about the needle 93, provide for a flat resting of the housing 89 on the insert 22.

The post 102 and end plate 103 are preferably part of a cap 104 which is mounted on the main portion 105 of the housing 89. This provides ease of construction since the needle 93 can be inserted into a bore 106 defined by the housing and having tapered open ends 107. The cap 104 is thereafter mounted on the housing main portion 105.

After the medical device 10 has been implanted in the patient, the connector assembly 88 can be mounted on the medical device as shown in FIGS. 4 and 5 and connected to a medication reservoir and pump system. Medication can then be given to the patient continously or intermittently without patient intervention.

Provision can also be made to have a sensor located on the exterior surface of the implant and having leads which are accessible on the supracutaneous portion of the implant. Those leads can then be connected to a microcomputer of an infusion device or to an appropriate monitoring system such as a meter or alarm device.

What is claimed is:

1. A medical device for percutaneous administration of medication comprising:
   (a) an implant having a supracutaneous portion and a subcutaneous portion defining a duct opening through the subcutaneous portion; the implant being adapted for implantation in the patient with the duct in fluid communication with a desired region of the patient and the supracutaneous portion exposed outside the patient;
   (b) an insert releasably and sealingly mounted on the implant supracutaneous portion; the insert including medication accepting means for placing the duct in sealed fluid communication with a medication source;
   (c) seal means carried by the implant and coacting with the insert for sealing the duct from the ambient surroundings outside the patient when the insert is removed from the implant; and
   (d) locking means for releasably retaining the insert on the implant, the locking means including a latch on one of the implant and insert, which latch is received in a detent defined by the other of the implant and the insert.

2. The medical device of claim 1 wherein the detent has a sloping surface to release the latch from the implant as the insert is rotated with respect to the implant.

3. The medical device of claim 1 wherein the insert includes a tubular body member having a proximal end and a distal end and defining a passageway; the insert also including a piercable and resealing septum sealing the passageway.

4. The medical device of claim 3 wherein the insert further includes an elastomeric flange extending about the proximal end of the tubular member, the flange cooperating and sealing with the implant supracutaneous portion.

5. A medical device for percutaneously delivering a medication to a patient comprising:
   (a) an implant having a supracutaneous portion defining a seat and a subcutaneous portion defining a cavity in fluid communication with the seat and a duct in fluid communication with the cavity, the duct opening through the subcutaneous portion; the implant being adapted to be implanted in the patient with the duct in fluid communication with the patient and the supracutaneous portion exposed outside the patient;
   (b) an insert releasably and sealingly mounted on the implant, the insert including a tubular body member received by the seat and having a proximal end and a distal end, the body defining a passageway in fluid communication with the cavity; the insert also including a pierceable and resealing septum mounted on the proximal end and sealing the passageway;
   (c) a closure carried in the implant cavity, coacting with the insert body member, and movable from first position to a second position; the closure being in the first position when the insert is mounted on the implant, and in the second position when the insert is removed from the implant; the closure, when in the first position, permitting fluid communication between the passageway and the cavity and, when in the second position, sealing the cavity and duct from the ambient surroundings outside the patient;
   (d) biasing means for maintaining the closure in the second position when the insert is removed from the implant; and
   (e) locking means for releasably retaining the insert on the implant, the locking means including a detent defined by the implant and a latch on the insert which is received in the detent.

6. The medical device of claim 5 wherein the closure includes a top plate and a generally frustoconical side wall which cooperates with a generally frustoconical sealing surface defined by the implant adjacent the seat.

7. The medical device of claim 5 wherein the biasing means includes a spring.

8. The medical device of claim 5 wherein the closure is within a region defined by the seat when in the second position and is spaced from the seat when in the first position.

9. The medical device of claim 8 wherein the latch includes a tab having a distal portion mounted on the body member and a proximal detent engaging portion biased away from the body member.

10. The medical device of claim 9 wherein the tab is unitary with the body member.

11. The medical device of claim 5 wherein the duct includes a flexible tube extending from the implant.

12. The medical device of claim 5 wherein the locking means releases the insert from the implant as the insert is rotated with respect to the implant.

13. The medical device of claim 5 wherein the insert further includes an elastomeric flange extending about the proximal end of the tubular member, the flange cooperatating and sealing with the supracutaneous portion of the implant about the seat.

14. The medical device of claim 13 wherein the septum and flange are unitary.

15. An insert for use with an implant defining a seat in fluid communication with a duct; the implant also including seal means for sealing the duct from the ambient atmosphere when the insert is removed from the implant, the insert comprising:
   (a) a tubular body member having a wall, a proximal end and a distal end and defining a fluid passageway, the body member also including an engagement surface adapted to coact with seal means when the insert is mounted on the implant to place the passageway in fluid communication with the duct;
   (b) a pierceable and resealing septum on the body member and sealing the passageway and
   (c) a latch on the tubular body member which cooperates with a detent on the implant to retain the insert on the implant.

16. The insert of claim 15 wherein the insert further includes an elastomeric flange about the proximal end of the body member, the flange being adapted to seal with the implant.

17. The insert of claim 16 wherein the septum and flange are unitary.

18. The insert of claim 15 wherein the latch includes a tab having a distal portion mounted on the body member and a proximal detent engaging portion biased away from the body member.

19. The insert of claim 18 wherein the body member wall defines a slot about the tab.

20. The insert of claim 15 wherein the passageway extends the length of the body member and the septum is mounted on the proximal end.

21. A medication delivery system for administrating medication to a patient from a medication reservoir, comprising:
   (a) a medical device including an implant defining a duct and a removable insert with a pierceable and resealing septum, the medical device being adapted to transcutaneous implantation in a patient with the duct in fluid communication with the patient and the septum exposed outside the patient, the medical device also including seal means for sealing the duct from the ambient surroundings outside the patient when the insert is removed from the implant; and
   (b) a connector assembly including a hollow piercing member mounted on a housing, the piercing member being in fluid communication with an inlet defined by the housing and adapted to be placed in sealed fluid communication with the medication reservoir; and attachment means for releasably mounting the connector assembly on the medical device with the piercing means penetrating the septum and placing the inlet in fluid communication with the duct.

22. The medical system of claim 21 wherein the implant is provided with a supracutaneous portion and with a subcutaneous portion defining the duct; the insert releasably and sealingly mounted on the implant supracutaneous portion and including a tubular body member having a proximal end and a distal end and defining a passageway in fluid communication with the duct; the septum being mounted on the proximal end of the body member and sealing the passageway.

23. The medical system of claim 21 wherein the attachment means provides for limited relative lateral float of the housing with respect to the septum to maintain proper alignment of the piercing member with the septum.

24. The medical system of claim 21 wherein the attachment means includes a coupling member having at least two legs which releasably grip the medical device.

25. The medical system of claim 24 wherein the coupling member includes a ring and at least two legs extending from the ring to grip the collar, the ring cooperating with and being restricted in its relative movement with respect to the housing by a post on the housing.

26. A medical system for delivery of a medication to a patient from a medication reservoir comprising:
   (a) a medical device including an insert releasably and sealingly mounted on an implant and a closure carried by the implant; the implant having a supracutaneous portion defining a seat and a subcutaneous portion defining a cavity in fluid communication with the seat and a duct in fluid communication with the cavity; the duct opening through the subcutaneous portion; the insert including a tubular body member received by the seat and having a proximal end and a distal end; the body defining a passageway in fluid communication with the cavity; the insert also including a piercable and resealing septum mounted on the proximal end and sealing the passageway; the closure being carried in the implant cavity, movable from a first position to a second position and coacting with the insert body member; the closure being in the first position when the insert is mounted on the implant and in the second position the insert is removed from the implant; the closure, when in the first position, permitting fluid communication between the passageway and the cavity and, when in the second position, sealing the cavity and duct from the ambient surroundings outside the patient; and
   (b) a connector assembly including a hollow piercing member and housing defining a channel and inlet with the channel in fluid communication with the inlet; the hollow piercing member being mounted on the housing in fluid communication with the channel; the connector assembly also including a coupling member movably mounted on the housing and permitting limited lateral movement of the housing with respect to the implant.

27. The medical system of claim 26 wherein the supracutaneous portion of the implant includes a collar and the coupling member grips the collar.

28. The medical system of claim 27 wherein the coupling member includes a ring and at least two legs extending from the ring to grip the collar, the ring cooperating with and being restricted in its relative movement with respect to the housing by a post on the housing.

29. A surgical implantable device for percutaneous administration of medication comprising:
   an implant having a supracutaneous portion and a subcutaneous portion defining a duct opening in the subcutaneous portion;
   a pierceable, self-sealing insert mounted in fixed operational position on the supracutaneous portion to seal the duct from the ambient surroundings, the insert being releasably retained on the supracutaneous portion;
   seal means reciprocably mounted in the implant and displaced by the insert to an operational position, the insert and seal means remaining fixed during operation wherein a cannula pierces the insert and injects medication through the duct;

bias means in the implant for automatically urging the seal means into a non-operational position to seal the duct from the ambient surroundings when the insert is removed from the implant; and locking means for releasably retaining the insert on the implant wherein the locking means includes a latch on one of the implant and the insert, which latch is received in a detent defined by the other of the implant and the insert.

30. The device of claim 29 wherein the seal means includes a closure biased toward a sealing surface defined by the implant.

31. The device of claim 30 wherein the closure includes a top plate, and a generally frustoconical side wall which cooperates with the sealing surface.

32. The device of claim 30 wherein the closure is biased toward the sealing surface by a spring.

33. The device of claim 29 wherein the implant supracutaneous portion defines a seat and the implant subcutaneous portion defines a cavity in fluid communication with the seat and duct.

34. The device of claim 33 wherein the seal means includes a closure positioned in the cavity and biased against a sealing surface defined by the implant.

35. The device of claim 29 wherein the locking means releases the septum from the implant as the septum is rotated with respect to the implant.

36. The device of claim 29 wherein the detent has sloping surface to release the latch from the implant as the septum is rotated with respect to the implant.

37. The device of claim 29 wherein the insert comprises a septum carried by a tubular body member, the tubular body member having a proximal end and a distal end and defining a passageway with the septum sealing the passageway.

38. The device of claim 37 wherein the septum includes a radial elastomeric flange, the flange cooperating and sealing with the implant supracutaneous portion.

* * * * *